United States Patent
Kim et al.

(10) Patent No.: US 8,716,029 B1
(45) Date of Patent: May 6, 2014

(54) CARBON NANOTUBE SENSORS EMPLOYING SYNTHETIC MULTIFUNCTIONAL PEPTIDES FOR SURFACE FUNCTIONALIZATION

(75) Inventors: Steve S. Kim, Dayton, OH (US); Zhifeng Kuang, Beavercreek, OH (US); Rajesh R. Naik, Dayton, OH (US); Barry L. Farmer, Xenia, OH (US)

(73) Assignee: The United States of America as represented by the Secretary of the United States, Washington, DC (US)

( * ) Notice: Subject to any disclaimer, the term of this patent is extended or adjusted under 35 U.S.C. 154(b) by 207 days.

(21) Appl. No.: 13/235,561

(22) Filed: Sep. 19, 2011

Related U.S. Application Data

(60) Provisional application No. 61/384,760, filed on Sep. 21, 2010.

(51) Int. Cl.
 *C12M 1/00* (2006.01)
(52) U.S. Cl.
 USPC .......................................................... 436/501
(58) Field of Classification Search
 None
 See application file for complete search history.

(56) References Cited

U.S. PATENT DOCUMENTS

| | | | |
|---|---|---|---|
| 6,528,020 B1 | 3/2003 | Dai et al. |
| 7,013,708 B1 | 3/2006 | Cho et al. |
| 7,112,816 B2 | 9/2006 | Schlaf et al. |
| 7,118,881 B2 | 10/2006 | Lee et al. |
| 7,247,877 B2 | 7/2007 | Hakey et al. |
| 7,276,088 B2 | 10/2007 | Huang et al. |
| 7,318,908 B1 | 1/2008 | Dai |
| 7,342,479 B2 | 3/2008 | Glatkowski et al. |
| 7,399,400 B2 | 7/2008 | Soundarrajan et al. |
| 7,452,528 B2 | 11/2008 | Huang et al. |
| 7,560,136 B2 | 7/2009 | Ward et al. |
| 7,569,850 B2 | 8/2009 | Noy et al. |
| 2003/0134267 A1 | 7/2003 | Kang et al. |
| 2003/0134433 A1 | 7/2003 | Gabriel et al. |
| 2004/0253741 A1 | 12/2004 | Star et al. |
| 2006/0040381 A1 | 2/2006 | Zhao et al. |

(Continued)

FOREIGN PATENT DOCUMENTS

| | | |
|---|---|---|
| WO | WO/02/31183 | 4/2002 |
| WO | WO/03/016901 | 2/2003 |
| WO | WO/2005/106760 | 10/2005 |
| WO | WO/2007/064355 | 7/2007 |

OTHER PUBLICATIONS

Kuang et al., Biomimetic chemosensor: designing peptide recognition elements for surface functionalization of carbon nanotube field effect transistors, Dec. 2009, ACS Nano, 4(1): pp. 452-458.*

(Continued)

*Primary Examiner* — Bao Thuy L Nguyen
*Assistant Examiner* — Richard Moerschell
(74) *Attorney, Agent, or Firm* — AFMCLO/JAZ; Rebecca Greendyke

(57) ABSTRACT

A biosensor that utilizes carbon nanotubes functionalized with a protein sequence. One domain of the multifunctional peptide sequence noncovalently binds to the surface of single-walled carbon nanotubes (SWNTs), while a second domain of the sequence recognizes and binds to a target molecule. The sequence of the peptide may be tailored to allow it to recognize and bind to specific target molecules, such as chemicals, biological materials, and explosives. The binding of the target molecule to the peptide may alter a material property of the SWNTs.

18 Claims, 5 Drawing Sheets

(56) References Cited

U.S. PATENT DOCUMENTS

| | | | |
|---|---|---|---|
| 2006/0115640 A1 | 6/2006 | Yodh et al. | |
| 2006/0172282 A1 | 8/2006 | Naik et al. | |
| 2007/0292896 A1 | 12/2007 | Strano et al. | |
| 2008/0044925 A1 | 2/2008 | Isojima et al. | |
| 2008/0058225 A1 | 3/2008 | Carlson | |
| 2008/0094078 A1 | 4/2008 | So et al. | |
| 2008/0176760 A1 | 7/2008 | Naik et al. | |
| 2008/0185295 A1* | 8/2008 | Briman et al. | 205/777.5 |
| 2008/0274912 A1 | 11/2008 | Johnson et al. | |
| 2008/0280780 A1 | 11/2008 | Hamers et al. | |
| 2009/0208922 A1 | 8/2009 | Choi et al. | |
| 2009/0227059 A1 | 9/2009 | Besnard et al. | |
| 2012/0156688 A1* | 6/2012 | McAlpine et al. | 435/7.1 |

OTHER PUBLICATIONS

Robert J. Chen et al, "Noncovalent Sidewall Functionalization of Single-Walled Carbon Nanotubes for Protein Immobilization," J. Am. Chem. Soc. vol. 123, pp. 3838-3839 (2001).

Robert J. Chen et al, "Noncovalent Functionalization of Carbon Nanotubes for Highly Specific Electronic Biosensors," PNAS, vol. 100 No. 9, pp. 4984-4989 (2003).

Erica S. Forzani et al, "Tuning the Chemical Selectivity of SWNT-FETs for Detection of Heavy-Metal Ions," Small, vol. 2 No. 11, pp. 1283-1291 (2006).

Sofia Sotiropoulou et al, "Carbon Nanotube Array-Based Biosensor," Anal Bioanal Chem vol. 375, pp. 103-105 (2003).

Kunjal Parikh et al, "Flexible Vapour Sensors Using Single Walled Carbon Nanotubes," Sensors and Actuators B vol. 113, pp. 55-63 (2006).

Ting Zhang et al, "Electrochemically Functionalized Single-Walled Carbon Nanotube Gas Sensor," Electroanalysis vol. 18 No. 12, pp. 1153-1158 (2006).

Chang-Soo Lee et al, "Electrically Addressable Biomolecular Functionalization of Carbon Nanotube and Carbon Nanofiber Electrodes," Nano Letters vol. 4 No. 9, pp. 1713-1716 (2004).

Alexander Star et al, "Gas Sensor Array Based on Metal-Decorated Carbon Nanotubes," J. Phys. Chem. B vol. 110, pp. 21014-21020 (2006).

J.P. Novak et al, "Nerve Agent Detection Using Networks of Single-Walled Carbon Nanotubes," Appl Phys Letters vol. 83 No. 19, pp. 4026-4028 (2003).

Kenzo Maehashi et al, "Label-Free Protein Biosensors Based on Aptamer-Modified Carbon Nanotube Field-Effect Transistors," Anal. Chem. vol. 79, pp. 782-787 (2007).

Keith Bradley et al, "Short-Channel Effects in Contact-Passivated Nanotube Chemical Sensors," Appl Phys Letters vol. 83 No. 18, pp. 3821-3823 (2003).

Robert J. Chen et al, "An Investigation of the Mechanisms of Electronic Sensing of Protein Adsorption on Carbon Nanotube Devices," J of Amer Chem Soc vol. 126, pp. 1563-1568 (2004).

Alexander Star et al, "Electronic Detection of Specific Protein Binding Using Nanotube FET Devices," Nano Letters, vol. 3 No. 4, pp. 459-463 (2003).

R. Martel et al, "Single- and Multi-Wall Carbon Nanotube Field-Effect Transistors," App Phys Letters, vol. 73 No. 17, pp. 2447-2449 (1998).

Pengfei Qi et al, "Toward Large Arrays of Multiplex Functionalized Carbon Nanotube Sensors for Highly Sensitive and Selective Molecular Detection," Nano Letters, vol. 3 No. 3, pp. 347-351 (2003).

Ningyi Liu et al, "Single-Walled Carbon Nanotube Based Real-Time Organophosphate Detector," Electroanalysis, vol. 19 No. 5, pp. 616-619 (2007).

Xiaowu Tang et al, "Carbon Nanotube DNA Sensor and Sensing Mechanism," Nano Letters, vol. 6 No. 8, pp. 1632-1636 (2006).

Hye Ryun Byon et al, "Network Single-Walled Carbon Nanotube-Field Effect Transistors (SWNT-FETs) with Increased Schottky Contact Area for Highly Sensitive Biosensor Applications," J Am. Chem. Soc., vol. 128 No. 7, pp. 2188-2189 (2006).

Alexander Star et al, "Label-Free Detection of DNA Hybridization Using Carbon Nanotube Network Field-Effect Transistors," PNAS, vol. 103 No. 4, 921-926 (2006).

Hye-Mi So et al, "Single-Walled Carbon Nanotube Biosensors using Aptamers as Molecular Recognition Elements," J. Am. Chem. Soc., vol. 127 No. 34, pp. 11906-11907 (2005).

Mehmet Sarikaya et al, "Molecular Biomimetics: Nanotechnology through Biology," Nature Materials, vol. 2, pp. 577-585 (2003).

Mark J. Pender et al, "Peptide-Mediated Formation of Single-Wall Carbon Nanotube Composites," Nano Letters, vol. 6, pp. 40-44 (2006).

Emmanuelle Danty et al, "Cloning and Expression of a Queen Pheromone-Binding Protein in the Honeybee: An Olfactory-Specific, Developmentally Regulated Protein," J. NeuroSci., vol. 19 No. 17, 7468-7475 (1999).

Audrey Lartigue et al, "Sulfur Single-Wavelength Anomalous Diffraction Crystal Structure of a Pheromone-Binding Protein from the Honeybee *Apis mellifera* L.," J. Biol. Chem., vol. 279 No. 6, pp. 4459-4464 (2004).

Gregg R. Dieckmann et al, "Controlled Assembly of Carbon Nanotubes by Designed Amphiphilic Peptide Helices," J. Am. Chem. Soc., vol. 125 No. 7, pp. 1770-1777 (2003).

Vasiliki Zorbas et al, "Importance of Aromatic Content for Peptide/Single-Walled Carbon Nanotube Interactions," J. Am. Chem. Soc., vol. 127 No. 35, pp. 12323-12328 (2005).

Justyn W. Jaworski et al, "Evolutionary Screening of Biomimetic Coatings for Selective Detection of Explosives," Langmuir, vol. 24, pp. 4938-4943 (2008).

* cited by examiner

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 1

His Ser Ser Tyr Trp Tyr Ala Phe Asn Asn Lys Thr
1               5                   10

<210> SEQ ID NO 2
<211> LENGTH: 4
<212> TYPE: PRT
<213> ORGANISM: Apis mellifera

<400> SEQUENCE: 2

Trp Phe Val Ile
1

<210> SEQ ID NO 3
<211> LENGTH: 20
<212> TYPE: PRT
<213> ORGANISM: Artificial Sequence
<220> FEATURE:
<223> OTHER INFORMATION: Recombinant sequence derived from Apis
      mellifera and an amino acid sequence generated in the laboratory
      by phage peptide display

<400> SEQUENCE: 3

His Ser Ser Tyr Trp Tyr Ala Phe Asn Asn Lys Thr Gly Gly Gly Gly
1               5                   10                  15

Trp Phe Val Ile
            20

<210> SEQ ID NO 4
<211> LENGTH: 4
<212> TYPE: PRT
```

```
-continued

<213> ORGANISM: Artificial Sequence
<220> FEATURE:
<223> OTHER INFORMATION: Generated by phage peptide display

<400> SEQUENCE: 4

Gly Gly Gly Gly
1
```

CARBON NANOTUBE SENSORS EMPLOYING SYNTHETIC MULTIFUNCTIONAL PEPTIDES FOR SURFACE FUNCTIONALIZATION

CROSS-REFERENCE TO RELATED APPLICATIONS

This application is related to, and claims priority from, co-pending U.S. Provisional Patent Application No. 61/384,760, filed on Sep. 21, 2010, by inventor Sang N. Kim, et al., and entitled "Nanotube Chemo/Bio Sensors Employing Multifunctional Peptides: Computational/Experimental Peptide Design and Device Fabrication," which is hereby incorporated herein by reference in its entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates to carbon nanotube-based sensors, and more particularly to sensors utilizing carbon nanotubes functionalized with a protein sequence containing a peptide recognition element.

2. Description of the Related Art

Carbon nanotubes are cylindrical tubes consisting entirely of carbon and are members of the fullerene structural family. The structure may be a single-walled carbon nanotube (SWNT), meaning that the nanotube wall comprises a single, one-atom thick layer of carbon arranged in a honeycomb crystal lattice, or it may be a multi-walled carbon nanotube comprising multiple layers of carbon tubes nested within one another. The small size and large surface area of carbon nanotubes allows them to possess unique electrical and mechanical properties, such as high thermal and electrical conductivity and high tensile strength. These unique properties have been used to develop rapid-response, SWNT-based sensors that are extremely sensitive, accurate, and light-weight.

Early carbon nanotube-based sensors took advantage of the SWNT's high propensity for molecular adsorption to create sensors that monitor the change in the nanotubes' electrical conductivity upon adsorption of a gas or liquid. However, these sensors generally possess poor selectivity as to the type of molecule adsorbed so that almost any gas or liquid alters the nanotubes' properties, thereby limiting the utility of these sensors.

More recently developed nanotube-based sensors possess increased selectivity due to chemical modification of the nanotubes or the application of functional coatings to the nanotube surface. These modifications to the SWNTs and the SWNT surface allow for increased selectivity and enhanced detection of specific chemical and biological species, while also reducing the amount of non-specific binding and adsorption that occurs. Nanotube-based sensors functionalized with naturally occurring biomolecules, such as enzymes and antibodies/antigens, often require an auxiliary mechanical or chemical linking mechanism to attach the functionalizing agent to the nanotube. The biomolecule alone is usually unable to bind to both the SWNT and the target molecule. In addition, many biomolecules are susceptible to loss of biological activity upon binding to a substrate such as a carbon nanotube and also to instability and degradation upon environmental exposure.

SUMMARY OF THE INVENTION

The present invention comprises a device for the selective detection of a target molecule. In one embodiment, the device comprises a plurality of single-wall carbon nanotubes having a first level of conductivity and a peptide sequence distributed on an outer surface of the single-wall carbon nanotubes. The peptide sequence may further comprise a first peptide domain that is capable of binding to at least a portion of the outer surface of the single-wall carbon nanotubes and a second peptide domain that is capable of selectively binding to the target molecule, wherein the single-wall carbon nanotubes have a second level of conductivity after binding of the target molecule to the second peptide domain. The target molecule may be at least one of an explosive, a chemical, and a biological molecule. The explosive may be trinitrotoluene.

The first peptide domain may comprise the sequence His-Ser-Ser-Tyr-Trp-Tyr-Ala-Phe-Asn-Asn-Lys-Thr (SEQ ID No. 1) and the second peptide domain may comprise the sequence Trp-Phe-Val-Ile (SEQ ID No. 2), wherein the second peptide domain is coupled to the first peptide domain by a sequence comprising Gly-Gly-Gly-Gly (SEQ ID No. 4). The first level of conductivity and second level of conductivity may further comprise at least one of thermal conductivity and electrical conductivity. The binding of the target molecule may be noncovalent such that the detection device may be reused by removing the target molecule from the second peptide domain.

In another embodiment, the device may further comprise a substrate, wherein the single-wall carbon nanotubes are distributed on a surface of the substrate. The substrate may comprise at least one of silicon, silicon dioxide, silicon nitride, aluminum oxide, and hafnium oxide. The single-wall carbon nanotubes may be distributed on a surface of the substrate using at least one of chemical vapor deposition, dielectrophoretic deposition, spray-painting, or drop-casting.

In another embodiment, the device may further comprise a sensing element that is capable of detecting a change from the first level of conductivity to the second level of conductivity.

In an alternative embodiment, the present invention comprises a reusable device for the selective detection of an explosive. The device may comprise a plurality of single-wall carbon nanotubes having a first level of electrical conductivity and a peptide sequence His-Ser-Ser-Tyr-Trp-Tyr-Ala-Phe-Asn-Asn-Lys-Thr-Gly-Gly-Gly-Gly-Trp-Phe-Val-Ile (SEQ ID No. 3) distributed on an outer surface of the single-wall carbon nanotubes. The peptide sequence may further comprise a first peptide domain His-Ser-Ser-Tyr-Trp-Tyr-Ala-Phe-Asn-Asn-Lys-Thr (SEQ ID No. 1) that is capable of binding to at least a portion of the outer surface of the single-wall carbon nanotubes and a second peptide domain Trp-Phe-Val-Ile (SEQ ID No. 2) that is capable of selectively binding to the target molecule, wherein the single-wall carbon nanotubes have a second level of electrical conductivity after the second peptide domain binds the target molecule. The explosive may be trinitrotoluene.

In another embodiment, the device further comprises a substrate, wherein the single-wall carbon nanotubes are distributed on a surface of the substrate. The substrate may further comprise a gate, a drain electrode, and a source electrode. Binding of the explosive may alter a source-drain current between the source electrode and the drain electrode.

In another embodiment, the gate may be a bottom-gate configuration. In another embodiment, the device may further comprise a reference electrode for monitoring an applied electrochemical potential, and the gate may be a liquid-gate configuration.

The device may further comprise a sensing element that is capable of detecting a change from the first level of conductivity to the second level of conductivity.

The present invention further includes a peptide for the detection of trinitrotoluene having an amino acid sequence comprising His-Ser-Ser-Tyr-Trp-Tyr-Ala-Phe-Asn-Asn-Lys-Thr-Gly-Gly-Gly-Gly-Trp-Phe-Val-Ile (SEQ ID No. 3), wherein the peptide sequence is capable of binding to a single-wall carbon nanotube.

Figure 1:
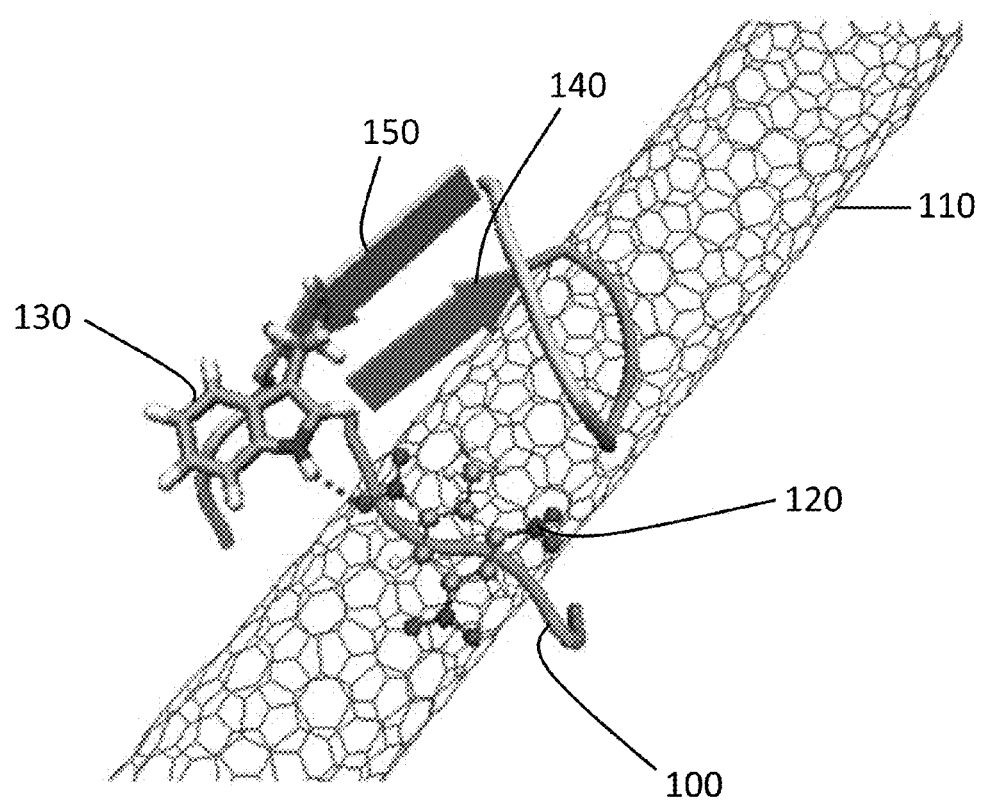
FIG. 1 is a perspective view of the predicted configuration of the P1ASP1C peptide upon binding to a SWNT and a target molecule.

SEQ ID No. 1 is the amino acid sequence of the carbon nanotube-binding domain.

SEQ ID No. 2 is the amino acid sequence of the target molecule-binding domain.

SEQ ID No. 3 is the amino acid sequence containing the carbon nanotube-binding and target molecule-binding domains with a tetraglycine linker.

SEQ ID No. 4 is the amino acid sequence used to link two peptide domains.

DETAILED DESCRIPTION OF THE INVENTION

The present invention provides a highly sensitive sensor that utilizes carbon nanotubes functionalized with a protein sequence. The multifunctional peptide sequence comprises one domain that noncovalently binds to the surface of single-walled carbon nanotubes (SWNTs), while a second domain recognizes and non-covalently binds to a target molecule. The sequence of the peptide may be tailored to allow it to recognize and bind to specific target molecules, such as chemicals, biological materials, and explosives, in particular trinitrotoluene. The binding of the target molecule to the peptide may alter a material property of the SWNTs, such as electrical or thermal conductivity, which may be harnessed to create a sensor. For example, a SWNT field effect transistor (FET) may be functionalized with one or more peptide sequences and placed into a sensor platform that monitors the source-drain current for changes in electrical conductivity. The disclosed invention is particularly useful for creating a sensor to monitor conditions at the nanometer scale.

Carbon nanotube-based sensors are a class of highly sensitive sensors that may be used to detect a variety of molecules. Biosensors may be created by coupling naturally occurring or synthetic biomolecules including nucleic acids, proteins, lipids, and other molecules produced by living organisms to carbon nanotubes to facilitate recognition and detection of chemical and biological molecules. Proteins demonstrate a high level of selectivity for specific target molecules, which makes them attractive candidates for carbon nanotube-based biosensors. However, proteins, like most biological molecules, may degrade upon exposure to environmental conditions. A protein's primary structure is its amino acid sequence; the secondary structure refers to localized structures such as α-helices and β-sheets; the tertiary structure is the three-dimensional shape of a single protein molecule; and the quaternary structure refers to the complex formed by the interaction of several protein molecules. The protein's ability to recognize and bind to a particular substrate, target molecule, or portion thereof depends upon its conformation, meaning its secondary, tertiary, and quaternary structure. The naturally existing, three-dimensional protein structure is called the native conformation. Outside the body, a protein may often exist in more than one conformation. In general, only a select few conformations are biologically active, meaning that the protein is able to recognize and bind to a target molecule.

Loss of protein function due to denaturation, misfolding, and other mechanisms may be the result of multiple environmental factors, including exposure to certain chemicals and changes in temperature, pH, or ionic concentration. In addition, binding of the protein to a substrate such as a SWNT often alters its tertiary or quaternary structure, which may alter, limit, or destroy the protein's activity. For example, studies have shown that proteins such as α-chymotrypsin undergo a conformational change upon binding to SWNTs, resulting in loss of protein activity.

As a result of these and other limitations, despite their high level of selectivity, proteins have generally not been a feasible choice as functionalizing agents for SWNT-based biosensors.

The presently disclosed invention solves these and other problems by providing a highly sensitive biosensor that utilizes SWNTs that have been functionalized with a stable peptide sequence. Unlike many other proteins and biomolecules, the currently disclosed peptide sequence demonstrates stability, making it feasible as a functionalizing agent. The peptide is long enough to maintain its high level of selectivity but short enough to avoid the problems of instability and degradation suffered by many larger protein molecules. The conformation of the P1ASP1C peptide upon binding to the SWNT surface is also such that the peptide recognition element is able to maintain selectivity toward the target molecule, while still remaining firmly bound to the SWNT. Unlike many other functionalized nanotube biosensors, the peptide disclosed in the present invention does not require an additional means of linking or binding the peptide to the surface of the SWNTs because the P1 domain is able to recognize and bind directly to the SWNT surface.

The following examples and methods are presented as illustrative of the present invention or methods of carrying out the invention, and are not restrictive or limiting of the scope of the invention in any manner.

Using phage peptide display screening or other known methods for selection of peptides with specific affinities, a peptide sequence that is capable of binding to the surface of SWNTs may be selected. A peptide with the sequence His-Ser-Ser-Tyr-Trp-Tyr-Ala-Phe-Asn-Asn-Lys-Thr (SEQ ID No. 1) was selected for its superior ability to bind to SWNTs. The sequence, which was named P1, was found to be capable of noncovalently binding to the surface of SWNTs. "Noncovalent" is defined as a chemical bond that does not involve the sharing of electrons but rather relies on molecular interactions such as hydrogen bonding, ionic interactions, hydrophobic interactions, and van der Waals forces. Covalent binding of the functionalizing molecule may affect the conductive properties of the SWNT and may thus alter its suitability for use as a sensor.

A second peptide sequence that is capable of recognizing and binding to the desired target molecule may also be selected. This second sequence is called the peptide recognition element. A protein was isolated from the antennae of honeybees bred and trained to detect explosives. In particular, a four amino acid sequence, Trp-Phe-Val-Ile (SEQ ID No. 2), was found to play an important role in the detection of explosives, particularly trinitrotoluene (TNT). This sequence was named the ASP1 sequence. The ASP1 peptide sequence was then fused to the P1 peptide via a tetraglycine linker (SEQ ID No. 4) to create a multifunctional peptide capable of binding to both the surface of the SWNTs and the target molecule. The peptide, with a sequence of His-Ser-Ser-Tyr-Trp-Tyr-Ala-Phe-Asn-Asn-Lys-Thr-Gly-Gly-Gly-Gly-Trp-Phe-Val-Ile (SEQ ID No. 3), was named P1ASP1C.

Initial predictions of the P1ASP1C peptide structure in solution and upon binding to a SWNT, a target molecule, or both may be obtained using molecular modeling software including modeling and wrapping programs developed by S. Maruyama, which are known in the art and commonly used. 1,289 possible structures were generated from the twenty peptide sequence. After determining five energy-minimized structures, replica exchange molecular dynamics (REMD) simulations were used to predict initial and equilibrated structures for each structure. Three different initial tertiary structures were predicted for the lowest energy structure, and upon equilibration, all three converged on a single, similar structure.

Referring to the drawings, like reference numerals may designate like or corresponding parts throughout the several views. FIG. 1 is a perspective view of the predicted structure of the P1ASP1C peptide 100 upon binding to a surface of a SWNT 110. As it is known that aromatic amino acids such as tryptophan (Trp), phenylalanine (Phe), and tyrosine (Tyr) aid in binding of a peptide sequence to the SWNT surface, the P1ASP1C peptide likely binds to the SWNTs via hydrogen bonding and π-π interactions. In particular, $Trp^5$ is believed to play a role in binding through π-π stacking. Substitution of $Trp^5$ with another amino acid such as alanine reduces the peptide's ability to bind to the SWNT. In addition, the conformation depicted in FIG. 1 allows the P1ASP1C peptide 100 to retain the β-sheet structures in the P1 domain (SEQ ID No. 1) 140 and the β-sheet structures in the ASP1C domain (SEQ ID No. 2) 150 that were predicted from the initial computational results (not shown). Also shown in FIG. 1 is a prediction of the non-covalent binding of a target molecule, TNT, 120 to $Trp^{17}$ 130.

To further determine the conformation of the P1ASP1C peptide upon binding to the SWNTs, circular dichroism (CD) spectroscopy and atomic force microscopy (AFM) were used to verify the computational results. CD spectroscopy was used to show that the P1ASP1C peptide took on a more ordered configuration when adsorbed to the SWNT surface by increasing the β-sheet fraction. AFM was used to determine that the protein uniformly coated the SWNT surface by showing a topological difference between the bare SWNTs and the functionalized nanotubes. A bare nanotube had a diameter of 1.4 (±0.25) nm. The SWNT functionalized with peptides had a diameter of 4.05 (±0.32) nm, indicating that the P1ASP1C peptide had coated the nanotubes with an estimated thickness of around 2.6 nm.

Adsorption of the P1ASP1C peptide (ligand) onto the SWNT (substrate) and interaction between the SWNT-P1ASP1C hybrid and various chemical agents was analyzed using known molecular dynamic modeling methods. For example, open source programs such as the AutoDock program (maintained by The Scripps Research Institute) are well-known and commonly used to predict binding of a ligand to a substrate and to evaluate the protein-protein interaction. The chemical analytes included 2,4,6-trinitrotoluene (TNT), an explosive; cyclotrimethylenetrinitramine (RDX), also an explosive; and 2-heptanone (HPT), an insect pheromone.

To estimate the relative binding affinity of various ligands to the functionalized SWNT substrate, the predicted structure of the P1ASP1C protein upon binding to the SWNT surface as shown in FIG. 1 was used to calculate the interaction energy in kcal/mol between the functionalized v. bare SWNT and three chemical compounds including TNT, RDX, and HPT. The interaction energy ($E_{interact}$) was calculated in a vacuum phase since the experiments were performed under vapor conditions. The interaction energy is defined as the difference of total potential energy before and after binding, where $E_{bond}$, $E_{angle}$, $E_{torsion}$, $E_{vdw}$, and $E_{ele}$ are the bond stretching, the angle bending, the torsion, the van der Waals interaction, and the electrostatic energy, respectively.

$$\Delta E_{interact} = E(\text{complex}) - E(\text{ligand}) - E(\text{substrate})$$

$$E = E_{bond} + E_{angle} + E_{torsion} + E_{vdw} + E_{ele}$$

Table 1 depicts the calculated interaction energy between the bare or functionalized SWNTs and the three chemical agents. The interaction energy between the RDX and HPT and the SWNT-P1ASP1C appeared similar to the interaction energy seen between the compounds and bare SWNTs that had not been functionalized with the P1ASP1C peptide, indicating that the compounds were migrating toward the bare nanotube surface rather than binding to the peptide. However, the SWNT-P1ASP1C hybrid was predicted to demonstrate a strong affinity for TNT and a higher interaction energy. See Table 1.

TABLE 1

| | Interaction Energy (kcal/mol) | |
| --- | --- | --- |
| Sample | SWNT | SWNT-P1ASP1C |
| TNT | −19 ± 1.15 | −28 ± 1.196 |
| RDX | −20 ± 1.36 | −21 ± 2.15 |
| HPT | −9 ± 0.62 | −9 ± 1.68 |

Figure 2A:
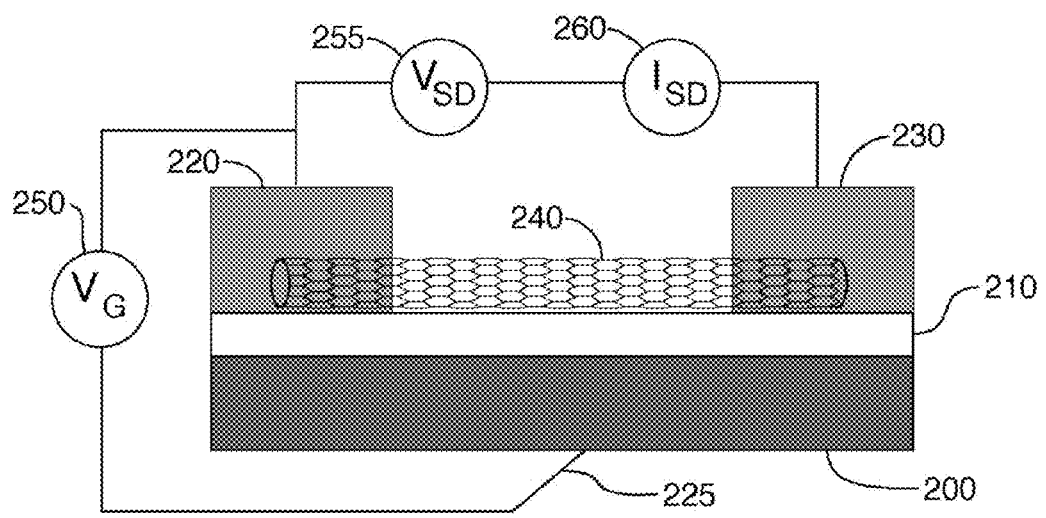
FIG. 2A is a side view of an exemplary bottom-gate field effect transistor device.

The predicted interactions may be further tested by placing the functionalized SWNTs into a sensor platform and measuring changes in the conductivity of the SWNTs upon binding of the target molecule. The P1ASP1C sequence described herein was tested by using a functionalized carbon nanotube field effect transistor (FET) that is exposed to TNT, RDX, and HPT. FIG. 2A is a side view of one embodiment of a back- or bottom-gate SWNT-FET device created in accordance with the disclosed invention. The device incorporates SWNTs 240 deposited onto a dielectric insulating layer 210, which sits atop a substrate 200. The substrate may comprise any commercially available thermally stable conducting layer such as doped silicon. Doping refers to the intentional introduction of impurities into a conductor or semiconductor for the purpose of modifying the material's conductivity. The dielectric insulating layer may be silicon dioxide ($SiO_2$), silicon nitride (SiN), or other suitable material, such as aluminum oxide ($Al_2O_3$) or hafnium oxide ($HfO_2$) having proper dielectric properties to be electrically insulating and thermally stable. Silicon wafers with 1 μm thermal oxide may be obtained commercially, for example, from University Wafers, Boston, Mass. A source electrode 220 and a drain electrode 230 sit atop the dielectric insulating layer 210, forming a channel in which the SWNTs 240 have been deposited. The electrodes may comprise chromium, gold, silver, copper, and other conductive materials or alloys thereof.

In the embodiment depicted in FIG. 2A, the dielectric insulating layer 210 and the substrate 200 serve as a gate 225. For optimal function of the device, the SWNTs 240 should be in full contact with the gate 225, the source electrode 220, and the drain electrode 230. When a gate-source voltage ($V_G$) 250 is applied between the gate 225 and the source electrode 220, a second voltage bias $V_{SD}$ 255 is given between the source electrode 220 and the drain electrode 230 as electrons flow between the two electrodes via the SWNTs 240, creating a source-drain current ($I_{SD}$) 260. The $I_{SD}$ 260 may be modulated by altering the $V_G$ 250. Binding of a target molecule such as TNT to the SWNTs 240 also alters the $I_{SD}$ 260. The configuration of the exemplary SWNT-FET device depicted in FIG. 2A may be used in sensors in a gaseous environment.

Figure 2B:
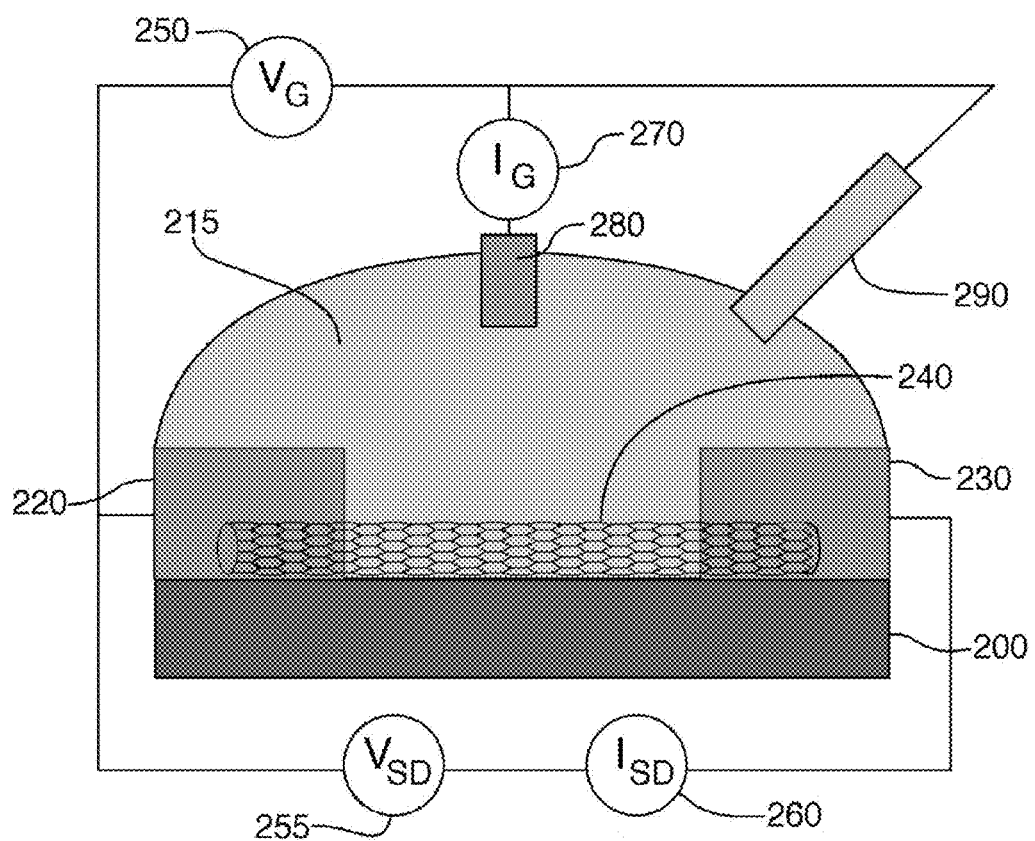
FIG. 2B is a side view of an exemplary liquid-gate field effect transistor device.

FIG. 2B is a side view of an alternative embodiment of the SWNT-FET device, a liquid-gate SWNT-FET configuration. The device incorporates SWNTs 240 deposited onto a substrate 200. For a liquid-gate device, the substrate may be an insulating material such as silicon dioxide ($SiO_2$), silicon nitride (SiN), or other suitable material, such as aluminum oxide ($Al_2O_3$) or hafnium oxide ($HfO_2$) having proper dielectric properties to be electrically insulating and thermally stable. A source electrode 220 and a drain electrode 230 sit atop the substrate 200 to form a channel. An aqueous buffer solution 215 surrounds the channel containing the SWNTs 240 and serves as the liquid gate. A gate electrode 280 serves as the voltage control to the liquid gate. The gate electrode may comprise platinum or other suitable conductive material. The reference 290 monitors an applied electrochemical potential. A gate-source voltage ($V_G$) 250 is applied to the gate electrode 280, which induces a gate current ($I_G$) 270 that is monitored to ensure the sensing signal is not from the electrochemical side reactions. A second voltage $V_{SD}$ bias 255 is created between the source electrode 220 and the drain electrode 230. Electrons flow from the source electrode 220 to the drain electrode 230 via the SWNTs 240, creating a source-drain current ($I_{SD}$). The $I_{SD}$ 260 may be modulated by altering the $V_G$ 250, and binding of a target molecule such as TNT to the SWNTs 240 also alters the $I_{SD}$ 260. The configuration of the exemplary SWNT-FET device depicted in FIG. 2B may be used in an aqueous environment.

The monolayer of networked SWNTs may be deposited on the substrate using carbon vapor deposition (CVD) or other suitable methods. The following is an exemplary CVD method. The wafer may be immersed in a 10 µM aqueous solution of iron hydroxide hexahydrate to allow nanoparticles of iron hydroxide to deposit on the thermal oxide layer contained on the substrate. The iron hydroxide catalyst may then be oxidized by exposure to air in an oven at a temperature of about 800° C. A 250 sccm Ar flow may be introduced for about 5 minutes, followed by a 500 sccm flow of $H_2$ as the temperature is raised to about 830° C. The Ar flow may be replaced by 250 sccm of $CH_4$ and 250 sccm of $H_2$ as the temperature is raised to about 900-1000° C. After about 20 minutes, growth of the nanotubes may be terminated by switching off the flow of $H_2$ and $CH_4$ and introducing a 150 sccm flow of Ar until the oven cools to room temperature. The density of SWNTs deposited onto the wafer may be controlled by adjusting the concentration of the iron hydroxide catalyst particles deposited on the thermal oxide layer. After deposition of the SWNT monolayer, conventional microlithography may be used to pattern an approximately 30/80 nm thick Cr/Au layer on top of the SWNT monolayer to create source and drain electrodes. Depending on the density of the nanotubes, the completed SWNT-FET device may have a channel width of about 2-100 micrometers between the source and drain electrodes.

The SWNT-FET device may also be fabricated by depositing the SWNTs onto a pre-assembled FET device. Commercially available SWNTs with enriched semiconducting content may be dispersed in an aqueous solution with the multifunctional peptides to allow functionalization of the SWNTs. The functionalized SWNTs may then be deposited onto the pre-assembled FET device using a dielectrophoresis field or other suitable method of deposition such as spray-painting and drop-casting. Dielectrophoretic deposition allows precise positioning and alignment of the SWNTs on the substrate. Alternatively, the SWNT-FET device may be fabricated using non-functionalized SWNTs. Commercially available SWNTs may be dispersed in an aqueous or organic solution and deposited onto the pre-assembled FET device using a dielectrophoresis field or other suitable method of deposition such as spray-painting and drop-casting. An aqueous solution of the multifunctional peptide may then be introduced into the channel containing the SWNTs to allow adsorption of the peptide onto the surface of the SWNTs in the SWNT-FET device. Both of these methods utilizing commercially available SWNTs allow for the rapid fabrication of mobile sensors in the field.

The multifunctional peptide may be commercially synthesized such that the termini are unblocked. The synthesized peptide may be stored as a dried powder or as an aqueous solution. Storage of the peptide as a dried powder provides additional stability in environments that may be detrimental to protein stability. To bind the peptide to the SWNT monolayer, an aqueous solution of about 0.2 mg/mL may be obtained by dissolving the dried peptide in deionized water or bringing an aqueous solution to the desired concentration. About 2 µL of the peptide solution may then be dropped on the channel containing the SWNTs, and after incubation for about 15 minutes in a 100% humidity chamber, the channel may be washed with deionized water and dried.

The binding of the target molecule to the functionalized SWNT-FET device was demonstrated in various environments, including vapor and aqueous. To test the response of the device in a gaseous environment, the SWNT-FET device was exposed to TNT (12 ppb), RDX (6.6 ppt), and HPT (2100 ppm) vapors in a chamber saturated with each vapor at 25° C., 1 atm. The response of the SWNT-FET device was monitored by tracking the source-drain current ($I_{SD}$). For example, a 4-probe station (MMR) equipped with a Keithley semiconductor parameter analyzer (SCS4200) may be used. As the device was exposed to the three chemicals, the source-drain current was monitored at a gate and source-drain bias voltage of −0.5 and 0.2V, respectively. Because of variations in the vapor pressure at the given experimental conditions, the selectivity of the functionalized SWNT-FET device was tested by comparing its response to that of the bare SWNT-FET device upon exposure to each chemical compound in turn.

Figure 3:
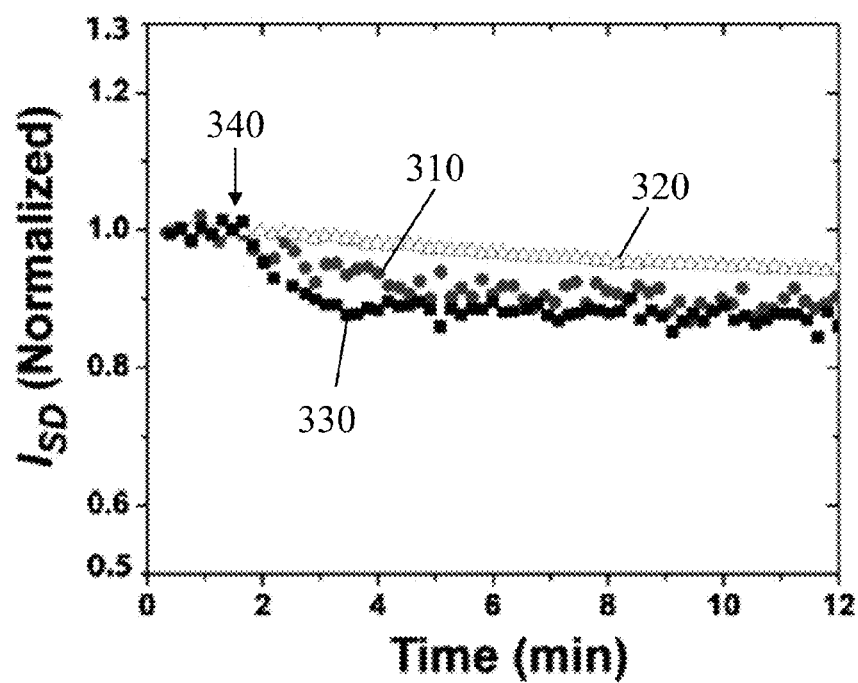
FIG. 3 is a graph depicting the interaction energy between a bare SWNT-FET and three chemical agents.

FIG. 3 is a graph of the response of the bare SWNT-FET device to TNT 310 (circles), RDX 320 (triangles), and HPT 330 (squares). After introduction of each respective vapor 340 into the chamber, the $I_{SD}$ of the bare SWNT-FET decreased upon exposure to both TNT 310 and HPT 330 but remained virtually unchanged upon exposure to RDX 320.

Figure 4:
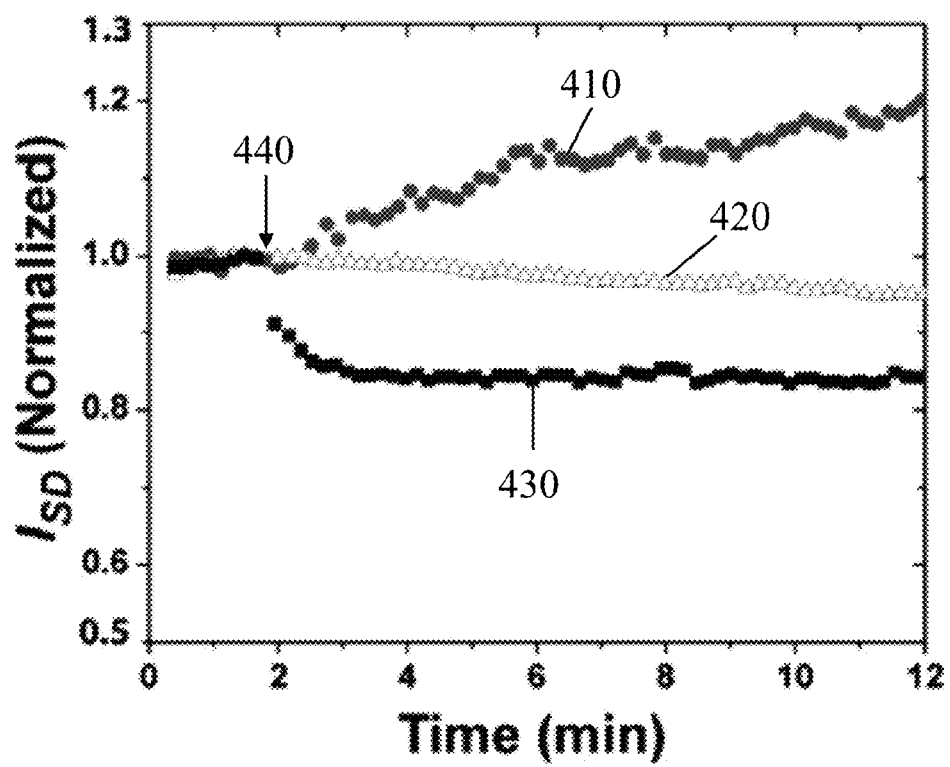
FIG. 4 is a graph depicting the interaction energy between a P1ASP1C-coated SWNT-FET and three chemical agents.

FIG. 4 is a graph of the response of the P1ASP1C-functionalized SWNT-FET device to TNT 410 (circles), RDX 420 (triangles), and HPT 430 (squares). After introduction of each respective vapor 440, the $I_{SD}$ of the functionalized SWNT-FET was monitored as before. Upon exposure to RDX 420, the $I_{SD}$ remained virtually unchanged, just as it had done in FIG. 3 with the bare SWNT-FET. Upon exposure to HPT 430, the functionalized SWNT-FET demonstrated a decrease in the $I_{SD}$ that was similar to that seen with the bare SWNT-FET in FIG. 3. However, the P1ASP1C-functionalized SWNT-FET device demonstrated a marked increase in its $I_{SD}$ upon exposure to TNT 410. These results demonstrate not only the selectivity and utility of the P1ASP1C-functionalized SWNT-FET sensor, but also the feasibility of using peptide sequences as surface coatings for carbon nanotube-based sensors.

The selective affinity of the P1ASP1C peptide for TNT was also demonstrated in an aqueous environment using surface plasmon resonance. Using a Biacore system, the peptide was immobilized on a CM5 Biacore chip using EDC/NHS coupling and blocked with ethanolamine. A TNT solution was made in 10 mM HEPES buffer, 150 mM sodium chloride, 3 mM EDTA, and 0.05% surfactant P20. The surface plasmon resonance response of P1ASP1C in the Biacore system showed that TNT could be detected in an aqueous environment at parts per trillion. The peptide demonstrated a strong affinity for TNT with a binding constant ($K_D$) of approximately 36 nM.

The change in source-drain current upon binding of TNT to the P1ASP1C peptide may be due to one of several phenomena. Adsorption of proteins at or near the junction of the SWNTs and the electrodes may cause a significant change in conductivity due to Schottky barrier modulation, which occurs when a metal contacts a semi-conductor. Another potential mechanism, chemical gating, involves changes in surface charge upon binding of the functionalizing protein to the target molecule.

The noncovalent nature of the binding between the TNT molecules and the P1ASP1C-functionalized SWNT-FET allows the sensor to be reused. For example, TNT removal may be accelerated by heating the sensor to 100-200° C. in ambient conditions. Optionally, a vacuum may be applied to the sensor at ambient temperature or during heating up to 600° C.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A device for selective detection of a target molecule, the device comprising:
    a plurality of single-wall carbon nanotubes having a first level of conductivity; and
    a peptide sequence distributed on an outer surface of the single-wall carbon nanotubes, the peptide sequence further comprising a first peptide domain that is capable of binding to at least a portion of the outer surface of the single-wall carbon nanotubes and a second peptide domain that is capable of selectively binding to the target molecule,
    wherein the single-wall carbon nanotubes have a second level of conductivity after binding of the target molecule to the second peptide domain
    wherein the first peptide domain comprises SEQ ID No.1 and the second peptide domain comprises SEQ ID No.2, wherein the second peptide domain is coupled to the first peptide domain by a sequence comprising SEQ ID NO.4.

2. The device of claim 1 wherein the target molecule is at least one of a chemical and a biological molecule.

3. The device of claim 2 wherein the chemical is an explosive, wherein the explosive is trinitrotoluene.

4. The device of claim 1 wherein the first level of conductivity and second level of conductivity further comprise at least one of thermal conductivity and electrical conductivity.

5. The device of claim 1 wherein the binding of the target molecule is noncovalent such that the detection device may be reused by removing the target molecule from the second peptide domain.

6. The device of claim 1 further comprising a substrate, wherein the single-wall carbon nanotubes are distributed on a surface of the substrate.

7. The device of claim 6 wherein the substrate comprises at least one of silicon, silicon dioxide, silicon nitride, aluminum oxide, and hafnium oxide.

8. The device of claim 6 wherein the single-wall carbon nanotubes are distributed on the surface of the substrate using at least one of chemical vapor deposition, dielectrophoretic deposition, spray-painting, or drop-casting.

9. The device of claim 1 further comprising a sensing element that is capable of detecting a change from the first level of conductivity to the second level of conductivity.

10. A reusable device for the selective detection of a chemical, wherein the chemical comprises an explosive, the device comprising:
    a plurality of single-wall carbon nanotubes having a first level of electrical conductivity; and
    a peptide sequence SEQ ID No. 3 distributed on an outer surface of the single-wall carbon nanotubes, the peptide sequence further comprising a first peptide domain SEQ ID No. 1 that is capable of binding to at least a portion of the outer surface of the single-wall carbon nanotubes and a second peptide domain SEQ ID No. 2 that is capable of selectively binding to the explosive, wherein the single-wall carbon nanotubes have a second level of electrical conductivity after the second peptide domain binds the explosive.

11. The detection device of claim 10 wherein the explosive is trinitrotoluene.

12. The device of claim 10 further comprising a substrate, wherein the single-wall carbon nanotubes are distributed on a surface of the substrate.

13. The detection device of claim 12 wherein the substrate further comprises a gate, a drain electrode, and a source electrode.

14. The device of claim 13 wherein the binding of the explosive alters a source-drain current between the source electrode and the drain electrode.

15. The device of claim 13 wherein the gate is a bottom-gate configuration.

16. The device of claim 13 wherein the device further comprises a reference electrode for monitoring an applied electrochemical potential, wherein the gate is a liquid-gate configuration.

17. The device of claim 10 further comprising a sensing element that is capable of detecting a change from the first level of conductivity to the second level of conductivity.

18. A peptide sequence for the detection of a chemical, wherein the chemical is trinitrotoluene, the peptide sequence comprising SEQ ID No. 3, wherein the peptide sequence further comprises a first peptide domain SEQ ID No. 1 that is capable of binding to at least a portion of an outer surface of a single-wall carbon nanotube and a second peptide domain SEQ ID No. 2 that is capable of selectively binding to the trinitrotoluene.

* * * * *